United States Patent [19]
Hill et al.

[11] Patent Number: 5,733,529
[45] Date of Patent: Mar. 31, 1998

[54] ULTRAMULSION BASED ANTIGINGIVITIS TOOTHPASTE COMPOSITIONS

[75] Inventors: Ira D. Hill, Locust; Peter P. Walters, Neshanic, both of N.J.; Dale G. Brown, Wharton, Tex.

[73] Assignee: WhiteHill Oral Technologies, Inc., Locust, N.J.

[21] Appl. No.: 461,698

[22] Filed: Jun. 5, 1995

[51] Int. Cl.$^6$ .................................................. A61K 7/16
[52] U.S. Cl. ................................................. 424/49
[58] Field of Search ........................................ 424/48, 49

[56] References Cited

U.S. PATENT DOCUMENTS

| | | | |
|---|---|---|---|
| 2,356,205 | 8/1944 | Blair et al. | 252/8.55 |
| 2,438,091 | 3/1948 | Lynch | 260/482 |
| 2,528,378 | 10/1950 | Mannheimer et al. | 260/309.6 |
| 2,658,072 | 11/1953 | Kosmin | 260/513 |
| 2,806,814 | 9/1957 | Richter | 167/93 |
| 2,826,551 | 3/1958 | Green | 252/89 |

(List continued on next page.)

FOREIGN PATENT DOCUMENTS

| | | |
|---|---|---|
| 689679 | 4/1953 | United Kingdom. |
| 849433 | 9/1960 | United Kingdom. |

OTHER PUBLICATIONS

Glantz et al., Arch. Oral Biol., 20:687–691, (1975).
Glantz et al., Acta. Odonot. Scand., 30:335–347 (1972).
Quirynen et al., J.Dent.Res., 68:796–799 (1989).
Pratt–Terpstra et al., J.Dent.Res., 68:463–467, (1989).
W. Zisman, Ind. Eng.Chem., 55:19–38 (1963).
R.Baier, Adhesion in Biological Systems, Academic Press, pp. 15–48 R.S. Manly (ed) (1970).
S.Friberg, Swed.Dent.J., 1:207–214 (1977).
Gaffar et al., Journal of Pharmaceutical Sciences, 74:1228–12332 (1985).
Gilbert et al., Caries Res. 21:29–36, (1987).
R.J. Gilbert, J. Pharm.Pharmacol., 39:480–3 (1987).
Waaler et al., J.Dent.Res., 101:192–5, (1993).
Addy et al., J.Clin. Periodontol., 17:693–7 (1990).
Jenkins et al., J.Clin. Periodontal., 18:145–8 (1991).
Jenkins et al., J.Clin. Periodontol., 16:385–387 (1989).
Rolla et al., Scand.J.Dent.Res. 101, 130–8 (1993).
Chemotherapy of Dental Plaque Infections, "Oral Sci. Ev., 9:65–107 (1976).
Becher P. in "Emulsions, Theory & Practice", (P.Becher, Ed.) p. 2, Rheinhold, New York, 1965.
Clayton, W., "The Theory of Emulsions and Their Technical Treatment", 4th Ed. p. 1, the Blakiston Co., Philadelphia, 1943.
Bancroft W.D., J. Phys. Phy. Chem., 17:501 (1913).
Prince, L.M. in "Microemulsion Theory & Practice", p. 2, Academic Press Inc., New York, NY (1977).

(List continued on next page.)

*Primary Examiner*—James J. Seidleck
*Assistant Examiner*—Michael A. Williamson
*Attorney, Agent, or Firm*—Ernest V. Linek

[57] ABSTRACT

The present invention relates to various toothpastes containing, stable, dispersions of certain high viscosity silicones in certain surfactants; wherein:

a. the dispersed silicones, which contain triclosan, 2,4,4'-triclosan-2'-hydroxy/epoxy/ether, are insoluble in said surfactant, are oriented by the surfactant such that when dispersed in water they are particularly adept at forming oriented, nonhelical coatings on surfaces of the mouth with enhanced substantivity, and b. the particle size of the dispersed silicone is from between about 0.1 and about 10 microns, with a particle size distribution such that from between about 80 and 95% of the dispersed silicone is within this particle size range. These stable dispersions are described as ULTRAMULSION dispersions, which, together with their physical properties, when contained in toothpastes, provide the toothpaste with enhanced with enhanced substantivity to mouth surfaces, where the non continuous silicone phase functions as a reservoir for the triclosan contained therein.

11 Claims, 4 Drawing Sheets

U.S. PATENT DOCUMENTS

| | | | |
|---|---|---|---|
| 3,254,714 | 6/1966 | Gogarty | 166/9 |
| 3,307,628 | 3/1967 | Sena | 166/9 |
| 3,433,780 | 3/1969 | Cekada, Jr. et al. | 260/29.2 |
| 3,497,006 | 2/1970 | Jones et al. | 166/273 |
| 3,506,070 | 4/1970 | Jones | 166/273 |
| 3,507,955 | 4/1970 | Osipow | 424/54 |
| 3,624,120 | 11/1971 | Yetter et al. | 556/425 |
| 3,964,500 | 6/1976 | Drakoff | 132/7 |
| 3,975,294 | 8/1976 | Dumoulin | 252/354 |
| 4,146,499 | 3/1979 | Rosano . | |
| 4,152,416 | 5/1979 | Spitzer et al. | 424/46 |
| 4,353,890 | 10/1982 | Scott | 424/49 |
| 4,364,817 | 12/1982 | Anderson et al. | 208/8 |
| 4,465,661 | 8/1984 | Schmolka | 424/49 |
| 4,476,107 | 10/1984 | Schmolka | 424/49 |
| 4,525,342 | 6/1985 | Weiss et al. . | |
| 4,537,778 | 8/1985 | Clipper et al. | 424/53 |
| 4,612,191 | 9/1986 | Yeh et al. | 424/52 |
| 4,620,878 | 11/1986 | Gee | 106/287 |
| 4,657,758 | 4/1987 | Goldemberg et al. | 424/49 |
| 4,661,341 | 4/1987 | Benedict et al. | 424/48 |
| 4,666,708 | 5/1987 | Goldemberg et al. | 424/49 |
| 4,774,077 | 9/1988 | Ferlando, Jr. | 424/82 |
| 4,894,220 | 1/1990 | Nabi et al. . | |
| 4,902,497 | 2/1990 | Crisanti et al. | 424/52 |
| 4,911,927 | 3/1990 | Hill et al. | 424/442 |
| 4,942,034 | 7/1990 | Hill et al. | 424/401 |
| 4,950,479 | 8/1990 | Hill et al. | 424/49 |
| 5,009,881 | 4/1991 | Hill et al. | 424/49 |
| 5,032,387 | 7/1991 | Hill et al. | 424/49 |
| 5,057,306 | 10/1991 | Hill et al. | 424/49 |
| 5,057,307 | 10/1991 | Hill et al. | 424/49 |
| 5,057,308 | 10/1991 | Hill et al. | 424/52 |
| 5,057,309 | 10/1991 | Hill et al. | 424/52 |
| 5,057,310 | 10/1991 | Hill et al. | 424/52 |
| 5,078,988 | 1/1992 | Lin | 424/49 |
| 5,098,711 | 3/1992 | Hill et al. | 424/401 |
| 5,165,913 | 11/1992 | Hill et al. | 424/49 |
| 5,284,648 | 2/1994 | White et al. | 424/49 |
| 5,380,530 | 1/1995 | Hill | 424/440 |
| 5,538,667 | 7/1996 | Hill et al. | 252/312 |

OTHER PUBLICATIONS

Prince, L.M. in "Biological Horizons in Surface Science", p. 361, Academic Press, Inc. (1973).

Eur. Poly. J., 26:654 (1990).

J. Chem. Phys., 49:1398 (1965).

J. Chem. Phys., 54:5011 (1971).

J. Chem. Phys., 59: 3825 (1973).

Macromolecules, 7:229 (1974).

Macromolecules, 11:627 (1978).

Journal of Society of Cosmetic Chemists, 25:609–619 (1974).

Journal of Colloid & Interface Science, 44:242–248 (1973).

Annals of the New York Academy of Science", Shulman & Montagne (1961).

Calandra et al., ACS Polymer Preprints, 17: 1–4 (1976).

Bass, Dent. Items of Interest, 70:921–34 (1948).

L. Menaker, The Biologic Basis of Dental Caries, Chapters 5, 11, 12, 14, 16 and 18, Harper & Row (1980).

ULTRAMULSION BASED ANTIGINGIVITIS TOOTHPASTE COMPOSITIONS

BACKGROUND OF THE INVENTION

The present invention relates to unique antigingivitis toothpaste compositions containing a dispersion of certain silicones in certain surfactants where the silicone has triclosan dissolved therein. When added to water these dispersions are stable and are distinct from solutions, emulsions and microemulsions. These dispersions are referred to hereinafter as ULTRAMULSION™ dispersions. This trademark is the property of Whitehill Oral Technologies, Inc. For further information regarding ULTRAMULSION™ dispersions, see copending application Ser. No. 08/144,778, now U.S. Pat. No. 5,538,667, the disclosure of which is hereby incorporated herein by reference. See also copending patent application Ser. Nos. 08/462,613; 08/462,203; 08/462,600; 08/463,010; 08/464,403; 08/462,599 and 08/462,930; all filed on Jun. 5, 1996, the disclosures of which are hereby incorporated by reference.

The ULTRAMULSION™ dispersion based antigingivitis toothpastes products of the present invention exhibit unique and unexpected substantivity to oral surfaces including teeth and gums while providing a reservoir for a lipid soluble active ingredient, triclosan, (2,4,4', -trichloro-2'-hydroxydiphenyl ether) resulting in antiplaque, antibacterial, antigingivitis benefits that last for extended periods. This combination of enhanced substantivity and the reservoir effect described in detail below are further combined with excellent particle size to provide optimum oral care coatings to the oral cavity.

Other oral care products containing the ULTRAMULSION™ dispersions of the present invention include: rinses, spray, gels, creams, other toothpastes, tooth powders, denture cleaning tablets, dental floss, interproximal simulators, mints, chewing gums, pet treats and pet main meals, as described in the referenced copending applications.

The antigingivitis toothpastes of the present invention may be prescription (Rx) products, i.e., those prescribed by dentists and hygienists in various professional oral hygiene treatments and/or may be over-the-counter (OTC) products used by patients under professional direction in various at-home self treatment programs and/or may be over-the-counter products used by consumers similar to anticaries toothpastes containing fluoride.

Retention of dental plaque to tooth surfaces plays an important role in the causation of both caries and periodontal disease. Periodontal disease especially has been associated for a long time with the adhering of dental plaque, and it has been shown that if this adhesion is prevented, the frequency of periodontal disease will decrease. "... controlling dental plaque through systematic use of tooth surface alteration agents ... could be useful." Glantz et al., *Dental Plaque Control, Measures & Oral Hygiene Procedures*, 185–194, IRL Press Lt. Oxford England (1980).

"Normal tooth surfaces have critical surface tension values ranging from about 32 dynes/cm to 50 dynes/cm. The bio-adhesive range has been described by Baier as a range of critical surface not attract microorganisms or other organic debris.... The bio-adhesive range of critical surface tension may be attained though the presence of selected lipid multilayers with carboxy group surfaces". ibid, p. 196. See also Glantz et al., *Arch. Oral Biol.*, 20: 687–691, (1975), R. Baier, *Surface Chemistry & Dental Integuments*, Charles C. Thomas, Springfield, Ill., 337–391, (1973); Glantz et al., *Acta. Odonot. Scand.*, 30: 335–347 (1972).

Rölla et al., *Biofouling*, 3: 175–181, (1991) reporting on "Plaque inhibition by changing the physical properties of the tooth surface", after referring to the work of Glantz & Alstrom, 1986, Quirynen et al., 1989 and Pratt-Terpstra et al., 1989 stated: "The authors have studied the interaction between polydimethylsiloxane and hydroxyapatite and also performed some clinical experiments examining this principle in test panels. It can be shown that the polydimethysiloxane is adsorbed strongly to the hydroxyapatite and enamel surface, probably due to its low surface tension, providing a hydrophobic layer on both. This hydrophobic surface was still able to bind protein (albumin) in vitro, but the protein was adsorbed by hydrophobic interactions rather than with normal electrostatic forces. Pellicle formation in vivo was delayed, and the nature of the pellicle was changed. The formation of plaque in vivo on polydimethylsiloxan-treated teeth was markedly reduced (FIG. 2 and the plaque which was accumulated appeared to be rather loosely bound to the tooth surfaces. This supports the concepts previously discussed by the authors: Zisman, 1963, Baier, 1970, Friberg, 1927, Glantz & Atlstrom, 1986. See also Glantz et al., *Dental Plaque Control, Measures & Oral Hygiene Procedures*, IRL Press, Loe H. & Kleinman D. (eds) Oxford, England 185–195, (1989). Quirynen et al., *J. Dent. Res.*, 68: 796–799 (1989), Pratt-Terpstra et al., *J. Dent. Res.*, 68: 463–467, (1989), W. Zisman, *Ind. Eng. Chem.*, 55: 19–38 (1963), R. Baier, *Adhesion in Biological Systems*, Academic Press, pp. 15–48, R. S. Manly (ed) (1970) and S. Friberg, *Swed. Dent. J.*, 1: 207–214, (1977).

For additional reference see: L. Menaker, "The Biologic Basis of Dental Caries," Chapters 5, 11, 12, 14, 16 and 18, Harper & Row (1980). See also U.S. Pat. Nos. 4,465,661; 3,507,955; 4,902,497; 4,661,341; 4,666,708; 4,537,778; 4,657,758; 3,624,120; 4,525,342; 4,476,107; 5,078,988; 2,806,814; 4,774,077; 4,612,191; 4,353,890; 4,894,220; British Patent No. 689,679, Gatter et al., *Journal of Pharmaceutical Sciences*, 74: 1228–1232 (1985); and Bass, *Dent. Items of Interest*, 70: 921–34 (1948).

Gilbert et al., *Caries Res.*, 21: 29–36, (1987) teaches oral reservoirs of triclosan are of potential importance to clinical studies of a triclosan-containing toothpaste and .... "These reservoirs are likely to exist in a number of sites in the mouth and may contribute to the therapeutic efficacy of such toothpastes."

Ellingsen et al., *Scand. J. Dent. Res.*, 102: 26–9, (1994) reports that "teeth topically treated with silicone oil and triclosan showed a marked plaque reduction, and those treated with silicone oil alone showed a moderate reduction as compared with a placebo .... It appears likely that this combination provides a reservoir of triclosan in the thin layer of silicone oil which binds strongly to teeth because of its low surface tension. Triclosan is then slowly released into saliva because of its low solubility in this fluid." See also Waaler et al., *J. Dent. Res.*, 101: 192–5, (1993). Gilbert et al., *J. Clin. Pharmacol.*, 23: 579–83, (1987). R. J. Gilbert, *J. Pharm. Pharmacol.*, 39: 480–3, (1987), Addy et al., *J. Clin. Periodontol.*, 17:693–7 (1990), Jenkins et al., *J. Clin. Periodontol*, 18: 145–8, (1991). Jenkins et al., *J. Clin. Periodontol*, 16: 385–387 (1989), Jenkins et al., *American Journal of Dentistry*, 2: 211–214, (1989).

Rölla et al., *Scand. J. Dent. Res.*, 101,130–2 (1993) reports "Deposition of a lipid soluble, antibacterial agent in a layer of silicone oil which adsorbs to the tooth surfaces because of its physical properties represents a new and promising principle in preventive dentistry."

The main cause of tooth loss in adults is periodontal disease. Yet, surprisingly, less than one percent of the public expenditures for dental treatment is for periodontal disease (see *J. Dent. Educ.*, 43: 320 (1979)). This is because conventional periodontal treatment is too expensive for most individuals, mainly due to the labor intensive, symptomatic treatment that is usually performed by highly skilled specialists.

Periodontal disease is an all-inclusive term for a variety of clinical entities that are forms of either gingivitis or periodontitis. Gingivitis is an inflammation of the gingiva or gums that can be associated with poor oral hygiene and/or hormonal states of the host. It is assumed, but not proven in the human, that gingivitis will progress to periodontitis, which is the form of the disease in which the infection has progressed to involve the oral tissues which retain the teeth in the jaw bone. Periodontitis is the more severe form of the disease, and if untreated, will eventuate in the loss of the tooth.

Dentists have long assumed that periodontal disease originates by the overgrowth of bacteria on the tooth surfaces in aggregates known as dental plaque. If this plaque persists for long periods of time on the tooth surfaces, it may in some instances calcify, forming the hard substance known as calculus. Numerous studies describe chemical agents which can in vitro and in vivo reduce plaque formation and calculus. However, none of these chemical agents has been reported to be successful in treating periodontitis.

Recent research in periodontal disease (see, for example, "Chemotherapy of Dental Plaque Infections," Oral Sci. Rev., 9: 65–107 (1976)) indicates that gingivitis and periodontitis are characterized by different types of bacteria. Gingivitis is associated with the accumulation of gram positive cocci and actinomyces, whereas periodontitis is characterized by proportional increases in anaerobic bacteria, such as spirochetes and black pigmented bacteroides (see "Host-Parasite Interactions in Periodontal Disease," R. J. Genco and S. E. Mergenhagen, eds. Amer. Soc. for Microbiol. Washington, D.C. p. 27–45, 62–75 (1982)). The different bacterial compositions of plaque associated with either gingivitis or periodontitis suggest that a mode of treatment that is effective in gingivitis may not be effective in periodontitis. Previous discoveries in the area of periodontal disease have assumed that there is no bacterial specificity in periodontal disease. This is now known to be incorrect. These bacterial differences in plaque may explain why an agent effective in plaque control, such as chlorhexidine, has little effect on gingivitis and no published effect on periodontitis.

Another important finding from recent periodontal research is that the composition of the dental plaque will differ according to its location on the tooth surface. Above the gingival or gum margin, facultative bacteria, such as gram positive cocci and rods, are numerically dominant, whereas below the gum margin, anaerobic motile bacteria such as spirochetes, and anaerobic gram negative rods including the black-pigmented bacteroides are predominant. In other words, two different microbial ecosystems are present on the same tooth surface.

Periodontal disease is a condition caused by a pathogenic microbial ecology established within the gingival sulcus which deepens to become a periodontal pocket. This microbial ecology, located deep within the periodontal pocket, differs greatly from that of the superficial oral environment by being more anaerobic, having a larger number of Gram negative organisms, and having a greater proportion of motile species.

Several factors impede the diffusion of medicinal agents when applied to the superficial periodontal tissues. Anatomically, the gum tissue is closely adapted to the neck of the teeth, mechanically restricting the diffusional pathway. In addition, a fluid termed gingival crevice fluid, with the approximate composition of plasma, permeates the periodontal environment and is continually produced by the diseased periodontal tissues at a rate of 10 to 100 microliters per hour. This fluid, emanating from the diseased pocket lining, creates a net outward flow further impeding the introduction of medications from superficially applied drug delivery devices. These interferences are sufficiently effective to insulate the pocket environment to the extent that saliva does not penetrate, and topically applied medicinal agents have been found largely ineffectual in the treatment of established periodontitis.

All of the foregoing references and the references cited in these references are incorporated in the description of the present invention.

ULTRAMULSIONS vs. EMULSIONS

The ULTRAMULSION™ dispersions of the present invention are distinct from other emulsions as will become apparent from the following:

When a system consists of a single liquid phase it is described as a solution. A system containing two or more liquid phases is described as a multiphase solution or emulsion.

According to Becher, an emulsion is an unstable heterogeneous system in which the diameters of the dispersed droplets in general exceed 1000Å. Becher P. in "Emulsions, Theory & Practice," (P. Becher, Ed.) page 2, Rheinhold, N.Y., 1965.

A more comprehensive definition of emulsion is advanced by Clayton: "An emulsion is a system containing two liquid phases, one of which is dispersed as globules in the other. The liquid which is broken up into globules is termed the dispersed or discontinuous phase, while the liquid surrounding the globules is known as the continuous phase or dispersing medium" Clayton, W., "The Theory of Emulsions and Their Technical Treatment," 4th Ed. page 1, the Blakiston Co., Philadelphia, 1943. It is well accepted that, mechanical work is required to affect such an emulsion, see Bancroft W. D., *J. Phys. Phy. Chem.*, 17:501 (1913).

According to Prince, an emulsion may be defined as a dispersion of two (or more) mutually insoluble liquids, one in the other. Because of the surface tension forces at play between the two liquids, the dispersed phase consists of spherical droplets. Prince, L. M. in "Microemulsion Theory & Practice," pg. 2, Academic Press Inc., New York, N.Y. (1977). See also Prince, L. M. in "Biological Horizons in Surface Science," pg. 361, Academic Press Inc. (1973).

Emulsions, are generally not stable and upon standing or after centrifuging tend to separate into two or more liquid layers.

The three definitions of emulsions set forth above share one common attribute, that is, mechanical work must be put into the emulsions described in order to disperse one liquid in the other in the form of droplets. This mechanical work can be in the form of agitation, homogenization, ultrasonication, etc.

In contrast, dispersions of very small droplet sizes which are formed spontaneously without the input of any mechanical work are called microemulsions. See Prince 1977, p. 3. Generally, two surfactants are used in forming microemulsions, i.e., a water soluble surfactant and a co-surfactant such as alcohol, where one phase of the microemulsion is generally water. Thus, dilution or adulteration of the dispersed phase by the co-solvent generally accompanies microemulsion formation. The ratio of surfactant to dispersed phase in microemulsions is much higher than that of emulsions. Microemulsions are further characterized as optically clear or opalescent and when spun in a laboratory centrifuge for 5 minutes at 100 G's, the dispersion remains stable and does not separate.

Thus, fine particle sizes, exceptional stability and rheological properties that can be easily adjusted, distinguish microemulsions from emulsions. Moreover, to date, no microemulsions have appeared in which one of the mutually insoluble liquids is not water. See Prince, page 34, (1977).

It has been surprisingly found that certain ULTRAMULSION™ dispersions, i.e., those of the present invention, provide various oral care products with improved antiplaque and antigingivitis, etc. performance attributed to: (a) their enhanced substantivity, (b) the reservoir effect achieved by solubilizing various lipid soluble active ingredients in the discontinuous silicone phase of the ultramulsion and (c) the generally small particle size of the dispersed silicone phase to effect suitable coatings in the oral cavity.

It is an object of the present invention to provide ULTRAMULSION™ dispersion-based antiplaque, antigingivitis toothpaste with enhanced substantivity while containing a reservoir of triclosan for treating gingivitis conditions.

It is another object of the invention to provide a method for manufacturing the ULTRAMULSION™ dispersion based toothpastes of the invention.

It is yet another object of the invention to provide a method to treat various gingivitis conditions with the ULTRAMULSION™ dispersion based toothpastes of the present invention.

It is another object of the present invention to provide ULTRAMULSION™ dispersion based toothpastes with improved oral care coating properties.

It is also an object of this invention to provide an ULTRAMULSION™ dispersion containing triclosan for toothpaste without the need to resort to use of complex high energy processes.

It is a further object of the present invention to provide ULTRAMULSION™ dispersion based toothpastes wherein lipid soluble triclosan is released from the ULTRAMULSION™ dispersion coating into the oral cavity over an extended period.

These and other objects will become readily apparent from the detailed description which follows.

Unless otherwise indicated, all percentages and ratios herein are by weight.

SUMMARY OF THE INVENTION

The ULTRAMULSION™ dispersion based toothpastes of the present invention combine certain characteristics of emulsions with certain features of microemulsions. That is, like emulsions, they are two phase systems comprising a silicone dispersed in a continuous, surfactant phase, wherein the silicone is insoluble in the surfactant. Unlike emulsions, but like microemulsions, these dispersions are stable. Unlike microemulsions, but like emulsions, mechanical work is required to form ultramulsions. Unlike microemulsions, but like emulsions, these ULTRAMULSION™ dispersions are not formed spontaneously. Like emulsions, the ULTRAMULSION™ dispersions do not contain a cosolvent commonly found in microemulsions. Of course, the ULTRAMULSION™ dispersion based toothpastes of the present invention are themselves stable dispersions in water-based toothpastes. See various examples below and the various tables below.

A random coil, helical, confirmation is characteristic of the semi-inorganic polymer chain, polydimethylsiloxanes, in the absence of solvents or diluents. In the helix the siloxane bonds are oriented towards the screw axis while the methyl groups point outward and shield the siloxane bond. This helical form is always the stable molecular confirmation when no external forces act on the siloxane chain. W. Moll, *Chemistry & Technology of Silicones*, Academic Press, New York, N.Y. 1968. See also, J. E. Mark, *Macromolecules*, 11:4, 627–633, 1978 and the references cited at pp. 632 and 633.

Polydimethylsiloxane polymer chains are considered semi-inorganic polymers since the chain backbone contains no C—C bonds.

It has been discovered this helical confirmation is not particularly suitable for coating oral surfaces. The present invention includes an uncoiling of this helix to promote improved coating of oral surfaces.

While not wishing to be bound by theory, it is hypothesized that unlike either emulsions or microemulsions, the dispersed silicones of the ULTRAMULSION™ dispersions of the present invention are uniquely uncoiled and oriented with their polar moieties in one general plane and their hydrophilic moieties in a plane approximately opposite that of the polar moieties. The helix configuration appears to uncoil into a zig-zag chain. This orientation promotes stability as well as bonding between the polar or hydrophilic moieties and various surfaces in the oral cavity thereby effecting enhanced substantivity, oriented, monolayer coatings of the silicone onto these surfaces. These oriented dispersions of silicones have a surprising utility in triclosan containing toothpastes as detailed in the various examples below. This orienting is illustrated in FIGS. 1 & 2.

The emulsifying effects of uncoiling of the helix configuration silicone molecule into a zig-zag chain with the oxygen moieties generally oriented in one plane distinct from that of the organo moieties as illustrated in FIGS. 1 and 2, are further substantiated by the following references: *Eur. Poly. J.*, 26:654 (1990); *J. Chem. Phys.*, 49: 1398 (1965); *J. Chem. Phys.*, 54: 5011 (1971); *J. Chem. Phys.*, 59: 3825 (1973); *Macromolecules*, 7: 229 (1974); *Macromolecules*, 11: 627 (1978) and "Rubber-Like Elasticity: A Molecular Primer," J. Mark, New York, Wiley-Interscience, 1988.

Methods of preparing polyorganosiloxane emulsions with an average particle size of less than about 0.3 microns and polyorganosiloxane microemulsions with an average particle size of less than about 0.14 micron are described in U.S. Pat. No. 4,620,878. Preparation of oil-in-water microemulsions are described in U.S. Pat. No. 4,146,499. Specific surface active compositions used as emulsifiers with diorganopolysiloxanes to form transparent microemulsions are described in U.S. Pat. Nos. 4,0562,331 and 3,975,294, U.S. Pat. No. 3,433,780 teaches the preparation of colloid silane suspensions. See also "Chemistry and Technology of Silicones," W. Noll, pp. 428 to 431 (1968); *Journal of Society of Cosmetic Chemists*, 25: 609–619 (1974) and *Journal of Colloid & Interface Science*, 44: 242–248 (1973).

Micellar dispersions, microemulsions, transparent emulsions are described in detail in "Annals of he New York Academy of Science", Shulman & Montagne (1961); U.S. Pat. No. 2,356,205, "The Theory of Emulsions & Their Technical Treatment," 5th Edition, 1954, U.S. Pat. Nos. 3,497,006; 3,506,070, 3,254,714 and 3,307,628.

The aqueous-free ULTRAMULSION™ dispersions of oriented silicones in surfactants where the silicone contains triclosan as described herein are neither taught nor suggested by the foregoing references.

DETAILED DESCRIPTION OF THE PREFERRED EMBODIMENTS

Figure 1:
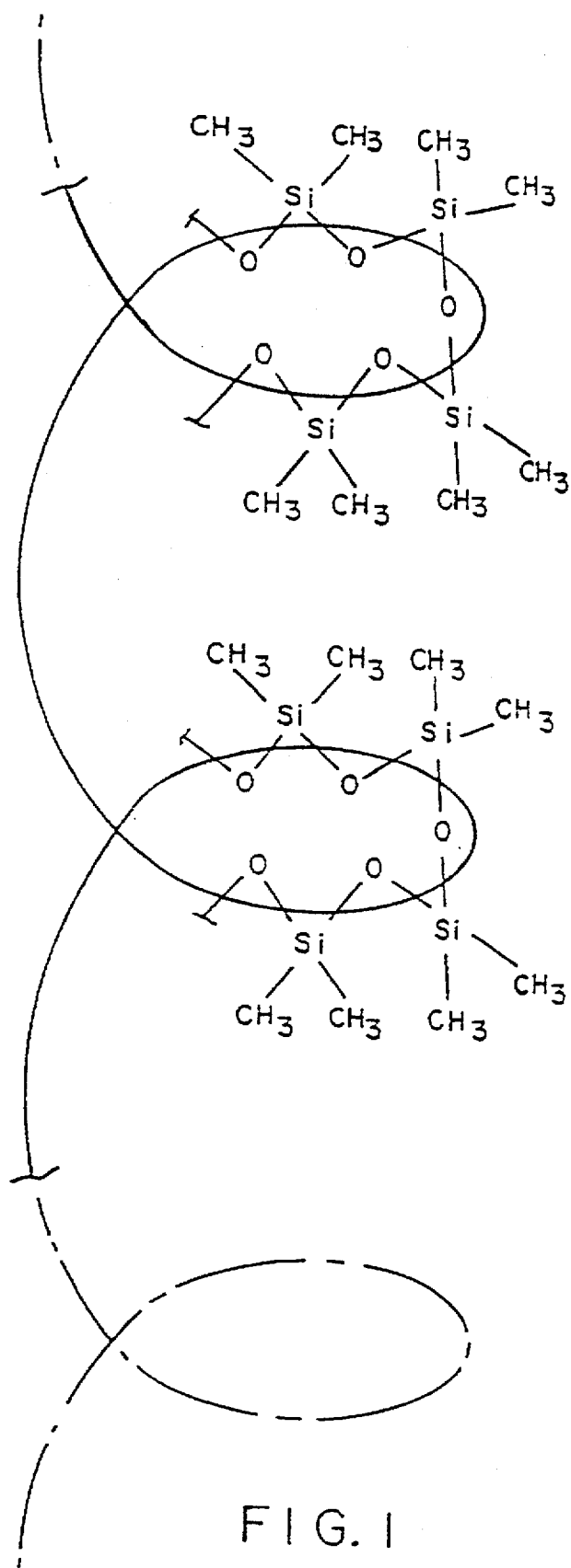
FIG. 1 illustrates the "coiled" molecular configuration proposed to polydimethylsiloxanes.

Referring to the drawings, FIG. 1 illustrates the accepted "coiled" configuration advanced for the semi-inorganic polymer, polydimethylsiloxanes, wherein the methyl moieties are oriented outward while the oxygen moieties are oriented inward towards the axis of the coil or helix. This configuration does not readily promote optimum "bonding" between the oxygen moieties and compatible surfaces such as those in the oral cavity.

Figure 2:
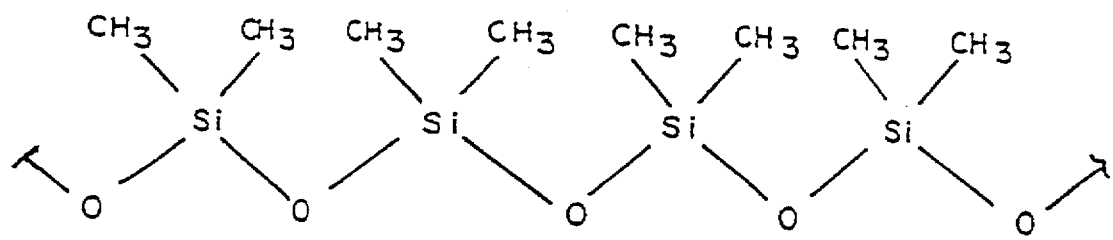
FIG. 2 illustrates the proposed zig-zag molecular configuration of oriented polydimethylsiloxanes after ULTRAMULSION™ dispersion processing.

FIG. 2 illustrates the "uncoiled oriented" configuration proposed for polydimethylsiloxanes that have been dispersed in the stable, ULTRAMULSION™ dispersion of the present invention, wherein the oxygen moieties are generally oriented in one plane distinct from that of the methyl moieties. This proposed uncoiled oriented configuration appears to support the unique and unexpected stability "bonding and enhanced substantivity" properties of the ULTRAMULSION™ dispersion of the present invention, and the reservoir effects achieved with triclosan contained in the dispersed silicone phase in various toothpaste preparations.

Figure 3:
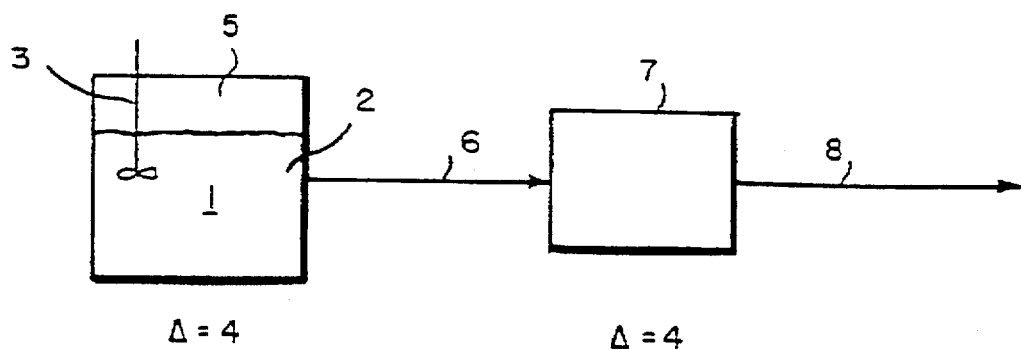
FIG. 3 illustrates schematically an ULTRAMULSION™ dispersion process of the invention.

FIG. 3 illustrates the ULTRAMULSION™ dispersion process of the present invention wherein a nonionic surfactant and a polydimethylsiloxane coating triclosan dissolved therein 1, substantially free from water and co-solvent, are mixed in vessel 2, provided with mixing means 3, heat source 4, and inert head space 5. The heated and mixed surfactant and poly-dimethylsiloxane/triclosan 6, is then subjected to high shear dispersion at an elevated temperature in dispersing means 7, to produce the ULTRAMULSION™ dispersion 8, suitable for inclusion in the toothpastes of the present invention.

Figure 4:
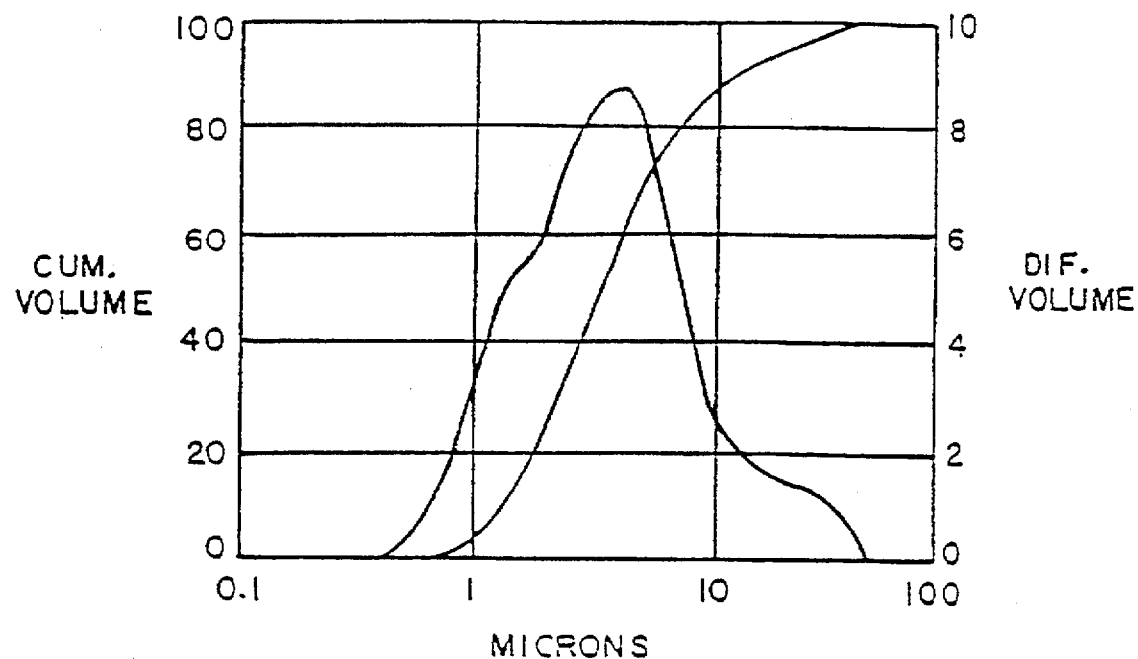
FIGS. 4 and 5 illustrate that the ULTRAMULSION™ dispersions of the invention produced via various high shear dispersing means having particle size distribution of 80+% under 10 microns.

FIG. 4 is a chart describing the particle size distribution of an ULTRAMULSION™ dispersion of the invention containing 95-5% by weight nonionic surfactant and 5-50% by weight polydimethylsiloxane (2.5 million cs) produced in a continuous process with an IKA Work dispersing means, (high shear dispersing) with an inlet temperature of 140° C. and an outlet temperature of 210° C.

Figure 5:
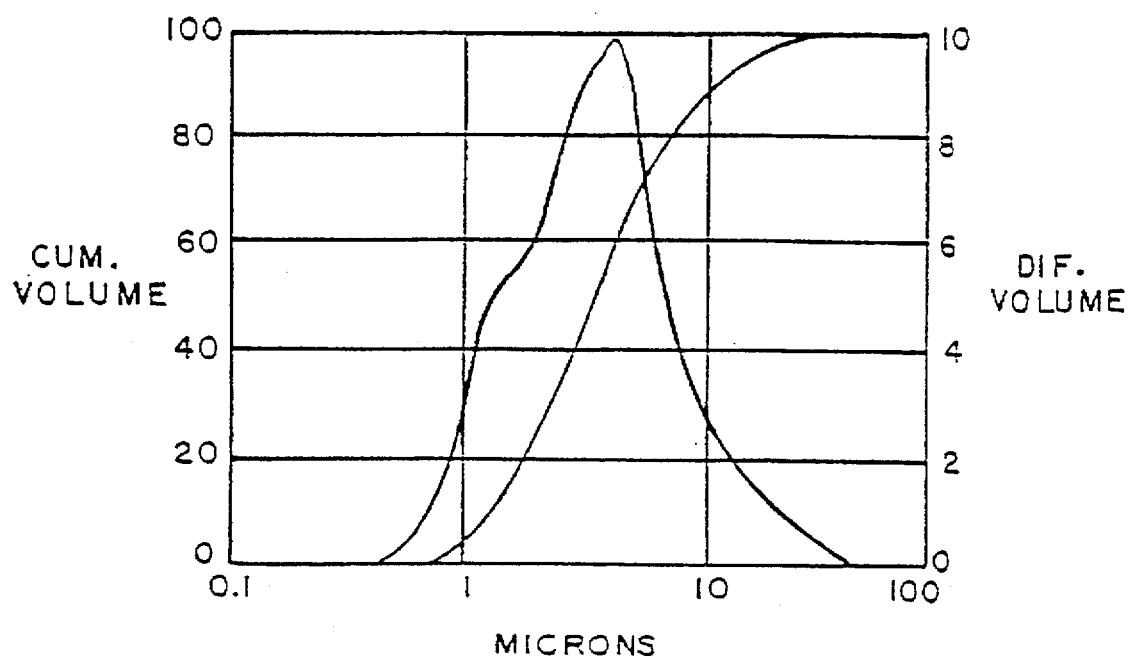

FIG. 5 is a chart describing the particle size distribution of an ULTRAMULSION™ dispersion of the invention containing 95-50% by weight nonionic surfactant and 5-50% by weight polydimethylsiloxane (2.5 million cs) produced in a batch process with a Ross M/E 100 LC dispersing means fitted with a 20 mesh screen, operated at a temperature from 120° to 160° C.

Figure 6:
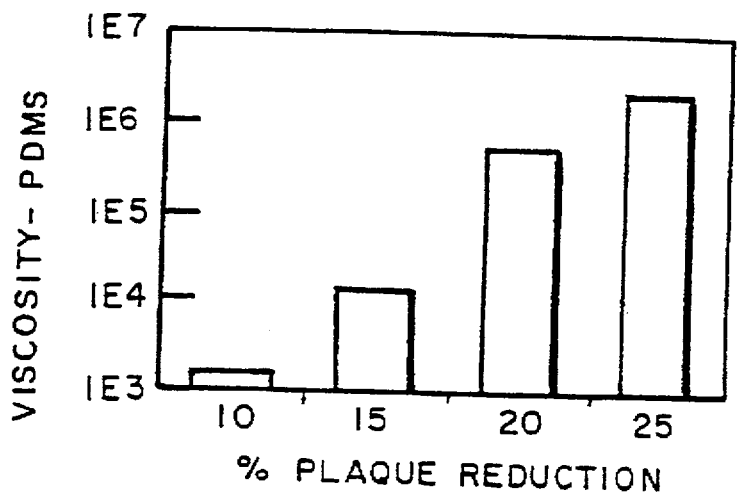
FIGS. 6 and 7 are a graph and a chart respectively showing the effect of increased silicone viscosity on plaque build-up in a certain oral care product.
Figure 7:
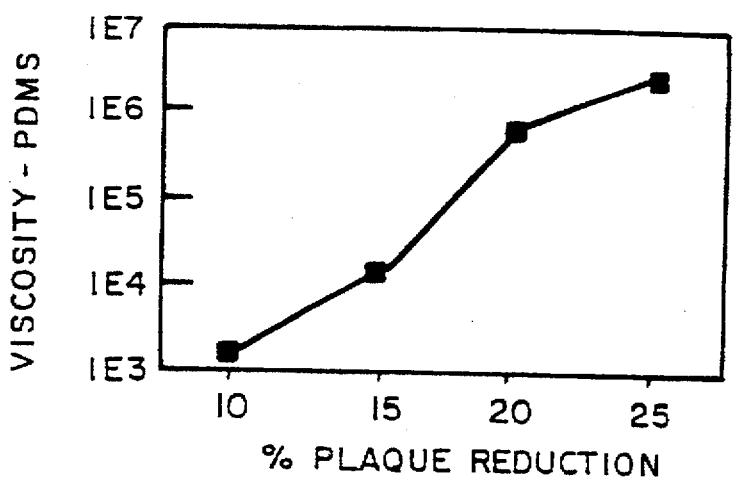

FIGS. 6 and 7 disclose the influence of increasing viscosity of the silicone in the ULTRAMULSION™ dispersion on the anti-plaque effect of this ULTRAMULSION™ dispersion when introduced into the oral cavity several times throughout the day as a mint. This reduction in plaque buildup is a substantial advance in establishing the efficacy and value of away-from-home oral care products such as mints.

The ULTRAMULSION™ dispersions of the present invention containing triclosan dissolved in the dispersed phase can be included in traditional toothpastes, to enhance the anti-plaque, and anti-gingivitis performance of such products as described in detail in the examples below.

These ULTRAMULSION™ dispersions containing triclosan in the dispersed silicone phase impart extended anti-plaque, anti-gingivitis effects to various toothpastes of the present invention. This "reservoir" effect of silicones containing active ingredients was documented with triclosan containing toothpaste by Rölla et al., in clinical studies reported in *Scand. J. Dent. Res.*, 101: 130–138 (1993).

It is suggested, that when the uncoiled zig zag structure of the polydimethylsiloxane containing triclosan is presented to the hydroxyapatite from a toothpaste of the present invention:

1. the polar siloxane moieties tend to bond with the hydroxyapatite leaving the methyl moieties available to interfere with the various bacterial actions that comprise plaque formation. Physical interference with plaque formation has been clinically established for coiled polydimethylsiloxane by Rölla (1993 and 1994);

2. the water soluble surfactant/triclosan present effects the bacteria present at the hydroxyapatite similar to those results reported for 0.3% triclosan containing products; and, 3. the lipid soluble triclosan contained in the dispersed silicone phase imparts an extended triclosan effect not only disrupting plaque but also producing an extended anti-gingivitis effect as the triclosan is released from the silicone coating throughout the coral cavity.

For purposes of the present invention, silicone means a clear, colorless substance containing polyalkylsiloxane polymers with average kinematic viscosities up to 50 million cs. Preferred high viscosity polydimethylsiloxanes have viscosities from between about 2.5 million cs and about 4 million cs and beyond including "gum" silicones having viscosities of 30 to 50 million cs; are particularly preferred for the oral care products, of the present invention. Other polydimethylsiloxanes suitable for the present invention include "substituted" water insoluble silicones and mixture's of polydiorganosiloxanes and substituted water insoluble silicones. specifically, water soluble silicones are excluded from the ULTRAMULSION™ dispersions of the invention. See Tables below.

The viscosity of some silicones can be measured by means of a glass capillary viscometer as set forth in Dow Corning Corporate Test Method CTM0004, Jul. 20, 1970. The viscosity in molecular weight relationship of silicones is described by Warwick et al., *Melt Viscosities of Dimethylpolysiloxanes,* Vol. 44, 5017, (October 1955).

The silicone fluid may be a high viscosity polyalkyl siloxane as described in detail below. Mixtures of various silicones may also be used and are preferred in certain embodiments of the invention.

References disclosing suitable silicone fluids include U.S. Pat. No. 2,826,551 to Green; U.S. Pat. No. 3,964,500 to Drakoff; U.S. Pat. No. 4,364,837 to Padner and British Patent No. 849,433 to Woolston. All of these patents are hereby incorporated herein by reference. Also incorporated herein by reference is *Silicon Compounds* distributed by Petrarch Systems, Inc., 1984. This reference provides a very good listing of suitable silicone materials.

Silicone materials found especially useful in the present compositions to provide good oral hygiene results are silicone gums. Silicone gums described by Petrarch and others including U.S. Pat. No. 4,152,416, May 1, 1979 to Spitzer et al., and Noll, Walter, *Chemistry and Technology of Silicones*, New York, Academic Press 1968. Also describing silicone gums are various General Electric Silicone Rubber Product Data Sheets. All of these described references are incorporated herein by reference. "Silicone gum" materials denote high molecular weight polydiorganosiloxanes having a viscosity up to about 50 million cs. Specific examples include polydimethylsiloxane, polydimethylsiloxane, methylvinylsiloxane, copolymer, poly(dimethylsiloxane, diphenyl, methvinylsiloxane copolymer and mixtures thereof.

As noted above high viscosity polydimethylsiloxanes i.e., those above 100,000 cs are preferred. Particularly preferred are polydimethylsiloxanes from between about 2.5 million cs and about 50 million cs. The safety of polydimethylsiloxanes for use in these various products is well documented. See Rowe et al., *Journal of Industrial Hygiene*, 30: 332–352 (1948). See also Calandra et al., "ACS Polymer Preprints," 17:1–4 (1976) and Kennedy et al., *J. Toxicol. & Environmental Health*, 1: 909–920 (1976).

As noted above, preferred polydimethylsiloxanes useful in the oral care compositions of the present invention are described as polymethylsiloxanes with the chemical composition:

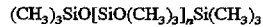

(CH$_3$)$_3$SiO[SiO(CH$_3$)$_3$]$_n$Si(CH$_3$)$_3$ wherein n is a whole number. These polydimethylsiloxanes have viscosities up to 50 million cs. and are generally described as having high molecular weights.

The particle size of the silicone in the ULTRAMULSION™ dispersion of the present invention can range from between about 0.1 and about 10 microns. In a preferred embodiment of the present invention the particle size of polydimethylsiloxanes in the ULTRAMULSION™ dispersion ranges from between about 1 and about 5 microns. The particle size distribution of the polydimethylsiloxanes in the ULTRAMULSION™ dispersion of the present invention generally range from between about 80 and about 95% of the particles under 10 microns. See FIGS. 4 and 5. In a preferred embodiment of the present invention, from between about 80 and about 95% of the particles are under 5 microns. See also Table 2.

An essential component of the ULTRAMULSION™ dispersion is a surfactant. The surfactant, may be selected from any of a wide variety of synthetic anionic, amphoteric, zwitterionic and nonionic surfactants, that are safe for use in the oral cavity.

The surfactants suitable for the purposes of the present invention must function as the continuous phase and contain the disposal discontinuous silicone phase. Generally, these surfactants are liquid or meltable substances and include mixtures of surfactants as detailed in the examples and tables below.

Synthetic anionic surfactants can be exemplified by the alkali metal salts of organic sulfuric reaction products having in their molecular structure an alkyl radical containing from 8–22 carbon atoms and a sulfonic acid or sulfuric acid ester radical (included in the term alkyl is the alkyl portion of higher acyl radicals). Preferred are the sodium, ammonium. potassium or triethanolamine alkyl sulfates, especially those obtained by sulfating the higher alcohols (C$_8$-C$_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxyl, sulfonate, sulfate, phosphate, or phosphonate. A general formula for these compounds is:

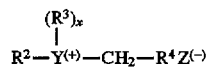

$$R^2-Y^{(+)}-CH_2-R^4Z^{(-)}$$

with $(R^3)_x$ on $Y$.

wherein R$^2$ contains an alkyl, alkenyl, or hydroxyl alkyl radical of from about 8 to 18 carbon atoms, from 0 to about 10 ethylene oxide moieties and from 0 to 1 glyceryl moiety; Y is selected from the group consisting of nitrogen, phosphorous, and sulfur atoms; R$^3$ is an alkyl or monohydroxyalkyl group containing 1 to about 3 carbon atoms; X is 1 when Y is a sulfur atom and 2 when Y is a nitrogen or phosphorous atom; R$^4$ is an alkylene or hydroxyalkylene of from 1 to about 4 carbon atoms and Z is a radical selected from the group consisting of carboxylate, sulfonate, sulfate, phosphonate, and phosphate groups.

Examples include:

4-[N,N-di(2-hydroxyethyl)-N-octadecylammonio]-butane-1-carboxylate;

5-(S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphate;

3-[N,N-dimethyl-N-hexadecylammonio-propane-1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and 5-(N,N-di(3-hydroxypropyl)-N-hexadecylammonio]-2-hydroxypentane-1-sulfate.

Other zwitterionics such as betaines are also useful in the present invention. Examples of betaines useful herein include the higher alkyl betaines such as cocodimethyl carboxymethyl betaine, lauryl dimethyl carboxymethyl betaine, lauryl dimethyl alphacarboxyethylene betaine, cetyl dimethyl carboxymethyl betaine, lauryl bis-(2-hydroxyethyl)carboxy methyl betaine, stearyl bis-(20-hydroxypropyl)-carboxymethyl betaine, oleyl dimethyl gammacarboxypropyl betaine, lauryl bis-(2-hydroxypropyl) alpha-carboxyethyl betaine, etc. The sulfobetaines may be represented by cocodimethyl sulfopropyl betaine, stearyl dimethyl sulfopropyl betaine, lauryl dimethyl sulfoethyl betaine, lauryl bis-(2-hydroxy-ethyl)sulfopropyl betaine and the like; amido betaines and amidosulfo betaines, wherein the $RCONH(CH_2)_3$ radical is attached to the nitrogen atom of the betaine are also useful in this invention. The amido betaines are preferred for use in some of the compositions of this invention. A particularly preferred composition utilizes an amido betaine, a quaternary compound, a silicone, a suspending agent and has a pH of from about 2 to about 4.

Examples of amphoteric surfactants which can be used in the ULTRAMULSION™ dispersion of the present invention are those which can be broadly described as derivatives of aliphatic secondary and tertiary amine in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylamino-propionate, sodium 3-dodecylamino-propane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, disobutylene, octane, or nonane, for example.

2. Those derived from the condensation of ethylene oxide with the product resulting from the reaction of propylene oxide and ethylenediamine products which may be varied in composition depending upon the balance between the hydrophobic and hydrophilic elements which is desired. For example, compounds containing from about 40% to about 80% polyoxyethylene by weight and having a molecular weight of from about 5,000 to about 15,000 resulting from the reaction of ethylene oxide groups with a hydrophobic base constituted of the reaction product of ethylene diamine and excess propylene oxide, said base having a molecular weight of the order of 2,500 to 3,000 are satisfactory.

3. The condensation product of aliphatic alcohols having from 8 to 18 carbon atoms, in either straight chain or branched chain configuration, ith ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

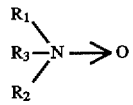

wherein $R_1$ contains an alkyl, alkenyl or monohydroxy alkyl radical of from about 8 to about 18 carbon atoms from 0 to about 10 ethylene oxide moieties, and from 0 to 1 glyceryl moiety, and $R_2$ and $R_2$ contains from 1 to about 3 carbon atoms and from 0 to about 1 hydroxy group, e.g., methyl, ethyl, propyl, hydroxy ethyl, or hydroxypropyl radicals. The arrow in the formula is a conventional representation of a semipolar bond. Example of amine oxides suitable for use in this invention include dimethyl-dodecylamine oxide, oleyldi(2-hydroxyethyl)amine oxide, dimethyloctylamine oxide, dimethyldecylamine oxide, dimethyltetradecylamine oxide, 3,6,9-trioxaheptadecyldiethylamine oxide, di) 2-hydroxyethyl)tetracylamine oxide, 2-dodecoxyethyldimethylamine oxide, 3-dodecoxy-2-hydroxypropyldi-(3-hydroxy-propyl)amine oxide, dimethylhexadecylamine oxide.

5. Long chain tertiary phosphine oxides corresponding to the following general formula:

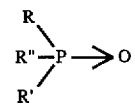

wherein R contains an alkyl, alkenyl or monohydroxyalkyl radical ranging from 8 to 18 carbon atoms in chain length from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyl-dimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyl-di(2-hydroxyl)phosphine oxide, stearyldimethylphosphine oxide, cetylethylpropylphosphine oxide, cetyldiethylphosphine oxide, dodecyldiethylphosphine oxide, tetradecyldiethylphosphine oxide, dodecyldipropylphosphine oxide, dodecyldi(2-hydroxyethyl)phosphine oxide, tetradecylmethyl-2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophosphic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl menthyl sulfoxide, 2-ketotridecyl methyl sulfoxide, 3,6,9, -trioxooctadecyl 2-hydroxyethyl sulfoxide, dodecyl menthyl sulfoxide, oleyl 3-hydroxypropyl sulfoxide, tetradecyl menthyl sulfoxide, 3-methoxytridecyl methyl sulfoxide, 3-hydroxytridecyl methyl sulfoxide, 3-hydroxy-4-dodecoxybutyl methyl sulfoxide.

Many additional nonsoap surfactants are described in McCUTCHEON'S, DETERGENTS AND EMULSIFIERS, 1979 ANNUAL, published by Allured Publishing Corporation which is incorporated herein by reference.

Particularly preferred nonionic surfactants are nonionic poloxamer surfactants of block copolymers of ethylene oxide and propylene oxide ranging from flowable liquids of varying viscosities, to paste, prills and cast solids with molecular weights from 1,100 to 150,000. Suitable nonionic surfactants are manufactured and marketed by BASF Corporation under the trademarks Pluronic. Particularly preferred nonionic surfactants are Pluronic F-68, F-88, F-108 and Pluronic F-127. These are described in a BASF brochure entitled "Pluronic and Tetronic Block Copolymer Surfactant." These nonionic surfactants suitable for the present invention can be described by the following structure:

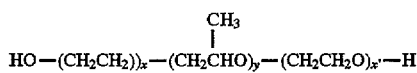

where x, y and x' are whole numbers. Surprisingly, the nonionic surfactants of choice for the ULTRAMULSION™ dispersion of the present invention are reported in the referenced brochure to have marginal detergency, emulsification and wetting properties. See Tables 1 and 2.

As noted above, the preferred nonionic poloxamer surfactants useful in the coating compositions of the present invention are described as polyoxyethylene-polyoxypropylene block copolymers such as Pluronic F-68, F-88, F-108 and F-127 (BASF) which have molecular weights of at least about 1000 such as described in U.S. Pat. Nos. 4,343,785, 4,465,663, 4,511,563 and 4,476,107, the disclosures of which are hereby incorporated herein by reference.

Emulsions of various coating substances including polydimethylsiloxanes in various surfactants including nonionic surfactants are disclosed and claimed in U.S. Pat. Nos. 4,911,927, 4,942,034; 4,950,479; 5,009,881; 5,032,387; 5,057,306; 5,057,307; 5,057;308, 5,057,309; 5,057,310, 5,098,711, 5,165,913 and 5,284,648. There is no teaching in these references that these highly viscosity silicone emulsions are stable nor that the "coating" substances are oriented as they are in the ULTRAMULSION™ dispersions of the toothpastes of the present invention.

The ratio of surfactant to silicone in the ULTRAMULSION™ dispersion based toothpastes of the present invention can range from between about 400:1 and about 1:2. In a preferred embodiment of the invention the ratio of surfactant to silicone is from between about 25:1 and 1:2. See Tables 1 and 2.

For the purposes of the present invention:
 a. stable is defined as, dispersion of the ULTRAMULSION™ dispersion in water when subjected to centrifuging in a 100 G environment for 5 minutes, less than about 10% by weight of the ULTRAMULSION™ dispersion separates from the continuous water phase and/or a substantial portion of the dispersed phase resists separation. This latter definition is particularly applicable to higher viscosity silicones. See Table 2.
 b. water-free means, that the ULTRAMULSION™ dispersion of silicone containing triclosan and surfactant is substantially free from water at the time it is formulated into the toothpastes of the present invention.
 c. solvent free means, that the ULTRAMULSION™ dispersion of silicone and surfactant in the toothpastes of the invention is substantially free from co-solvents such as ethanol, isopropanol, etc.
 d. oriented means, that the polar moieties of the "uncoiled" polydimethylsiloxane containing triclosan in the ULTRAMULSION™ dispersion based toothpastes are generally aligned in one plane with the hydrophilic oil seeking moieties aligned in a second plane such as illustrated in FIG. 2.
 e. monolayer means, that the monomolecular film of the ULTRAMULSION™ dispersion released from the toothpaste of the invention when dispersed in water is attracted to mucosa and hydroxyapatite by secondary bonding forces to form a substantive coating thereon.

The ULTRAMULSION™ dispersions of the present invention are prepared as follows:

Generally, if not a liquid, the surfactant is heated to a temperature at which it becomes a liquid. The silicone coating triclosan dissolved therein is dispersed in the heated surfactant with various high shear dispersing means.

Specifically the heated surfactant is mechanically stirred along with the silicone, to which has previously been added the triclosan, to form a pre-emulsion mixture in which the silicone/triclosan is uniformly dispersed in the surfactant in droplets of a larger size then desired for the ULTRAMULSION™ but small enough to optimize the subsequent high shear dispersions. This mixture is subjected to high-shear dispersions with a means such as the IKA-WORKS DISPAX-Reactor with at least one superfine generator, alternatively, a Ross Model M.E., 100 LC fitted with a 20 mesh screen or a ultrasonicator such as MEDSONIC XL2010 fitted with 800-C Flow Cell & 800-21CT ¾ inch flanged horn can be used.

Various ULTRAMULSION™ dispersions suitable for the toothpastes of the present invention, which are prepared and analyzed are described in detail in the examples below.

TABLE I

ORAL CARE
% W/W

| Component | Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Dimethicone viscosity-centistokes | | | | | | | | | | | |
| 100,000 | 10 | — | — | — | — | — | — | — | — | 33 | — |
| 600,000 | — | 10 | — | — | — | — | 33 | — | — | — | — |
| 2,500,000 | — | — | 10 | — | — | — | — | 33 | — | — | 10 |
| 4,000,000 | — | — | — | 10 | — | — | — | — | 33 | — | — |
| 30,000,000 | — | — | — | — | 10 | — | — | — | — | — | — |
| 50,000,000 | — | — | — | — | — | 10 | — | — | — | — | — |
| Triclosan | 1 | 2 | 3 | 4 | 5 | 6 | 2 | 4 | 6 | 8 | 10 |
| Poloxamer - 188 | — | — | — | — | — | — | — | — | — | 59 | — |
| Poloxamer - 238 | — | — | — | — | — | — | — | — | — | — | 80 |
| Poloxamer - 338 | 89 | 88 | 87 | 86 | 85 | 84 | — | — | — | — | — |
| Poloxamer - 407 | — | — | — | — | — | — | 65 | 63 | 61 | — | — |

Specific poloxamer/polydimethylsiloxane ULTRAMULSION™ dispersions suitable for use with various toothpaste preparations were prepared and analyzed as described in Table 2 below:

TABLE 2

ORAL CARE % W/W

| Component | Example No. | | | | | | | | | |
|---|---|---|---|---|---|---|---|---|---|---|
| | 12 | 13 | 14 | 15 | 16 | 17 | 18 | 19 | 20 | 21 |
| Dimethicone viscosity-centistokes | | | | | | | | | | |
| 600,000 | — | 11.6 | — | — | — | 10.0 | — | — | — | — |
| 2,500,000 | 10.0 | — | — | 11.9 | 11.9 | — | — | — | — | 14.0 |
| 4,000,000 | — | 11.6 | — | — | — | — | — | — | — | — |
| 30,000,000 | — | — | 10 | — | — | — | — | — | 11.6 | — |
| 50,000,000 | — | — | — | — | — | — | 11.6 | 10.0 | — | — |
| Lipid Soluble | | | | | | | | | | |
| Triclosan | 10 | 1.16 | 1.16 | 1.3 | 1.0 | 1.75 | 1.16 | 1.16 | 5 | 2.0 |
| Surfactant | | | | | | | | | | |
| Poloxamer 338 | 80.0 | 75.64 | 88.84 | 86.8 | 87.15 | 88.25 | 87.24 | 88.84 | 83.4 | 84.0 |

The discontinuous silicone phase of the ULTRAMULSION™ dispersion based toothpastes can also contain a wide range of lipid soluble and/or lipid dispersible oral care ingredients ranging from antimicrobials to desensitizing/ substances, to healants such as aloe to vitamins such as vitamin E, to flavorants, etc. These various ingredients in the silicone phase of the ULTRAMULSION™ dispersion based toothpastes of the present invention perform similar to the triclosan, i.e., as though they are contained in a "reservoir". These various lipid soluble substances in the silicone phase continue to be available at the ULTRAMULSION™ dispersion oral surface interface as long as the ULTRAMULSION™ dispersion coating remains substantive to mouth surfaces. Effects attributed to this "reservoir" are described by Rölla et al., supra.

The toothpastes containing the ULTRAMULSION™ and triclosan dispersions of the present invention will contain a variety of essential components ranging from surfactants and abrasives for cleaning, to whiteners, to gelling aids to flavorants etc. These are detailed in various Examples described below.

Water is an essential component of the toothpastes of the present invention which contain one or more of the various ULTRAMULSION™ dispersions described above. The water in these products is generally present at a level of from about 20% to about 95%, preferably from between about 60% and about 90%.

In addition these toothpastes of the invention can contain a variety of nonessential optional components suitable for rendering such compositions more acceptable. See Tables 3 to 6 below.

Such conventional optional ingredients are well known to those skilled in the art, e.g., preservatives such as benzyl alcohol, methyl paraben, propyl paraben and imidiazolidinyl urea; cationic surfactants such as cetyl trimethylammonium chloride, lauryl trimethyl ammonium chloride, tricetyl methyl ammonium chloride, stearyldimethyl benzyl ammonium chloride, and di(partially hydrogenated tallow) dimethylammonium chloride; thickeners and viscosity modifiers such as diethanolamide of a long chain fatty acid (e.g., PEG 3 lauramide), block polymers of ethylene oxide and propylene oxide such as Pluronic F88 offered by BASF Wyandotte, sodium chloride, sodium sulfate, polyvinyl alcohol, and ethyl alcohol; pH adjusting agents such as citric acid, succinic acid, phosphoric acid, sodium hydroxide, sodium carbonate, etc., perfumes; dyes; and, sequestering agents such as disodium ethylenediamine tetraacetate. Such agents generally are used individually at a level of from about 0.01% to about 10%, preferably from about 0.5% to about 5.0% by weight of the composition.

The pH of the present compositions is preferably from 6 to 8.

METHOD OF MANUFACTURE

The various toothpastes of the present invention can be made by mixing the materials together and heating if necessary and following accepted manufacturing practices for these various products as described in detail below.

INDUSTRIAL APPLICABILITY

The toothpastes of the present invention have utility in a wide range of specific toothpastes as illustrated below.

The Examples set forth in Tables III through VII further describe and demonstrate preferred embodiments within the scope of the present invention. The Examples are given solely for the purpose of illustration and are not to be construed as limitations of the present invention as many variations thereof are possible without departing from its spirit and scope.

TABLE III

TOOTHPASTE COMPOSITIONS % W/W

| Component | Example # 22 | 23 | 24 | 25 | 26 | 27 | 28 | 29 | 30 | 31 | 32 | 33 |
|---|---|---|---|---|---|---|---|---|---|---|---|---|
| Dicalcium Phosphate Dihydrate | 49.0 | 49.0 | 49.0 | 49.0 | 49.0 | 49.0 | 49.0 | 49.0 | 49.0 | 49.0 | 49.0 | 49.0 |
| Sorbitol - 70% Aq. | 18.0 | 18.0 | 18.0 | 18.0 | 18.0 | 18.0 | 18.0 | 18.0 | 18.0 | 18.0 | 18.0 | 18.0 |
| Water | 16.67 | 16.67 | 16.67 | 16.67 | 16.67 | 16.67 | 16.67 | 16.67 | 16.67 | 16.67 | 16.67 | 16.67 |
| Glycerine | 10.0 | 10.0 | 10.0 | 10.0 | 10.0 | 10.0 | 10.0 | 10.0 | 10.0 | 10.0 | 10.0 | 10.0 |
| SodiumCarboxyMethyl Cellulose | 1.0 | 1.0 | 1.0 | 1.0 | 1.0 | 1.0 | 1.0 | 1.0 | 1.0 | 1.0 | 1.0 | 1.0 |
| Flavor | 1.0 | 1.0 | 1.0 | 1.0 | 1.0 | 1.0 | 1.0 | 1.0 | 1.0 | 1.0 | 1.0 | 1.0 |
| Sodium Lauryl Sulfate | 0.8 | 0.8 | 0.8 | 0.8 | 0.8 | 0.8 | 0.8 | 0.8 | 0.8 | 0.8 | 0.8 | 0.8 |
| Titanium Dioxide | 0.5 | 0.5 | 0.5 | 0.5 | 0.5 | 0.5 | 0.5 | 0.5 | 0.5 | 0.5 | 0.5 | 0.5 |
| Sodium MonoFluoroPhosphate | 0.76 | 0.76 | 0.76 | 0.76 | 0.76 | 0.76 | 0.76 | 0.76 | 0.76 | 0.76 | 0.76 | 0.76 |
| Sodium Saccharin | 0.27 | 0.27 | 0.27 | 0.27 | 0.27 | 0.27 | 0.27 | 0.27 | 0.27 | 0.27 | 0.27 | 0.27 |
| ULTRAMULSION ™ (See Table I) | | | | | | | | | | | | |
| Example 1 | 2.0 | — | — | — | — | — | — | — | — | — | — | — |
| Example 3 | — | 2.0 | — | — | — | — | — | — | — | — | — | — |
| Example 6 | — | — | 2.0 | — | — | — | — | — | — | — | — | — |
| Example 4 | — | — | — | 2.0 | — | — | — | — | — | — | — | — |
| Example 7 | — | — | — | — | 2.0 | — | — | — | — | — | — | — |
| ULTRAMULSION ™ (See Table II) | | | | | | | | | | | | |
| Example 12 | — | — | — | — | — | 2.0 | — | — | — | — | — | — |
| Example 14 | — | — | — | — | — | — | 2.0 | — | — | — | — | — |
| Example 15 | — | — | — | — | — | — | — | 2.0 | — | — | — | — |
| Example 16 | — | — | — | — | — | — | — | — | 2.0 | — | — | — |
| Example 17 | — | — | — | — | — | — | — | — | — | 2.0 | — | — |
| Example 18 | — | — | — | — | — | — | — | — | — | — | 2.0 | — |
| Example 21 | — | — | — | — | — | — | — | — | — | — | — | 2.0 |

In addition to the foregoing, other toothpastes are included in the present invention including whitening toothpastes, toothpastes for treating hyposensitivity, toothpastes for dry mouth sufferer, toothpastes for patients undergoing radiation therapy, etc.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A stable aqueous based toothpaste composition containing dispersed therein an ULTRAMULSION dispersion comprising a nonionic poloxamer surfactant and a polydimethylsiloxane containing triclosan insoluble in said surfactant wherein:

a. said polydimethylsiloxane has the chemical composition $(CH_3)_3SiO[SiO(CH_3)_2]_nSi(CH_3)_3$, wherein n is a whole number;

b. said surfactant has the chemical composition

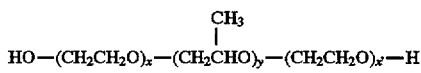

wherein x, y, and x' are whole numbers;

c. the viscosity of the polydimethylsiloxane ranges from between about 2.5 million and about 50 million cs;

d. the particle size of greater than 50% of the polydimethylsiloxane in the ULTRAMULSION dispersion is from between about 0.1 and about 10 microns;

e. the triclosan is present at a concentration from between about 0.1 and about 0–6% by weight;

f. from between about 80% and 95% of said polydimethylsiloxane particles in the ULTRAMULSION dispersions are from between about 1 and about 10 microns;

g. the nonionic surfactant is a polyoxyethylene-polyoxypropylene block copolymer having a molecular weight from between about 1,100 and about 150,000; and h. the ratio of surfactant to polydimethylsiloxane is from between about 400:1 and about 1:2.

2. A toothpaste composition according to claim 1, wherein the ratio of said surfactant to said polydimethylsiloxane is 9:1 and 90% of the polydimethylsiloxane particles are from between about 1 and 3 microns and the triclosan level is from between about 0.1 and about 0.6%.

3. A toothpaste composition according to claim 1, wherein the ratio of said surfactant to said polydimethylsiloxane is 2:1 and 100% of the polydimethylsiloxane dispersion is less than 10 microns and the triclosan level is from between about 0.2 and about 0.5%.

4. A toothpaste composition according to claim 1, wherein the ratio of said surfactant to said polydimethylsiloxane is 1:1 and the polydimethylsiloxane particles in said ULTRAMULSION dispersion are less than 10 microns.

5. A toothpaste composition according to claim 1, wherein the polydimethylsiloxane is uncoiled and oriented wherein the oxygen moieties are generally oriented in a plane distinct from that of the methyl moieties.

6. A toothpaste composition according to claim 1, wherein the surfactant is selected from the group consisting of, flowable liquids of varying viscosities, pastes, prills and cast solids.

7. A toothpaste composition according to claim 1, wherein the ratio of surfactant to polydimethylsiloxane is 1:1 and at least 80% of the polydimethylsiloxane dispersed particles are between 1 and 9 microns.

8. A toothpaste composition according to claim 1, wherein the ratio of surfactant to polydimethylsiloxane is 9:1 and about 90% of the polydimethylsiloxane dispersed particles are between 1 and 3 microns.

9. A toothpaste composition according to claim 1, wherein the ratio of surfactant to polydimethylsiloxane is 2:1 and about 90% of the polydimethylsiloxane dispersed particles are between 1 and 3 microns.

10. A toothpaste composition according to claim 1, wherein the ratio of surfactant to polydimethylsiloxane is 4:1 and about 90% of the polydimethylsiloxane dispersed particles are between 1 and 9 microns.

11. A toothpaste composition according to claim 1, wherein the ratio of surfactant to polydimethylsiloxane is 9.5:0.5 and about 100% of the polydimethylsiloxane dispersed particles are between 1 and 9 microns.

* * * * *